(12) United States Patent
Lampropoulos

(10) Patent No.: US 7,591,805 B2
(45) Date of Patent: Sep. 22, 2009

(54) INTEGRAL FLUSHING DEVICE

(75) Inventor: Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 990 days.

(21) Appl. No.: 10/800,071

(22) Filed: Mar. 11, 2004

(65) Prior Publication Data

US 2005/0203463 A1    Sep. 15, 2005

(51) Int. Cl.
*A61M 5/00*    (2006.01)
(52) U.S. Cl. ...................................... 604/187
(58) Field of Classification Search ............... 604/181, 604/183, 187, 218, 235, 246, 247, 264, 266, 604/267, 275, 30, 35
See application file for complete search history.

(56) References Cited

U.S. PATENT DOCUMENTS

| | | | |
|---|---|---|---|
| 3,628,523 A * | 12/1971 | Pirtle, Jr. .................... 600/432 |
| 3,635,218 A * | 1/1972 | Ericson ........................ 604/37 |
| 4,332,254 A | 6/1982 | Lundquist .................. 128/344 |
| 4,668,217 A | 5/1987 | Isono .......................... 604/49 |
| 5,290,222 A | 3/1994 | Feng et al. .................... 604/86 |
| 5,320,613 A | 6/1994 | Houge et al. ................ 604/283 |
| 5,651,372 A * | 7/1997 | Caillouette .................. 600/567 |
| 5,827,236 A | 10/1998 | Takahashi ................... 604/240 |
| 5,855,568 A | 1/1999 | Battiato et al. .............. 604/240 |
| 5,984,897 A * | 11/1999 | Petersen et al. ............. 604/187 |
| 6,146,362 A | 11/2000 | Turnbull et al. ............. 604/256 |
| 6,616,634 B2 * | 9/2003 | Benz et al. .................. 604/187 |
| 6,830,563 B1 * | 12/2004 | Singer ........................ 604/181 |

* cited by examiner

*Primary Examiner*—Manuel A Mendez
(74) *Attorney, Agent, or Firm*—Ryan D. Benson; Stoel Rives LLP

(57) ABSTRACT

The present invention relates to a flushing device having simple operation and one-handed control. The flushing device utilizes a plunger for expelling a flushing medium from the barrel of the flushing device configured such that the user can actuate the plunger easily with the user's palm and/or with other portions of the user's hand. The flushing device includes a receiving tip which has a distal end and a proximal end, the inner diameter of the distal end of the receiving tip being larger than the inner diameter of the proximal end of the receiving tip. The receiving tip is non-opaque (i.e. clear, translucent) to allow the user to view insertion of the catheter tip. The flushing device includes one or more finger grips positioned distally from a middle portion of the barrel.

31 Claims, 6 Drawing Sheets

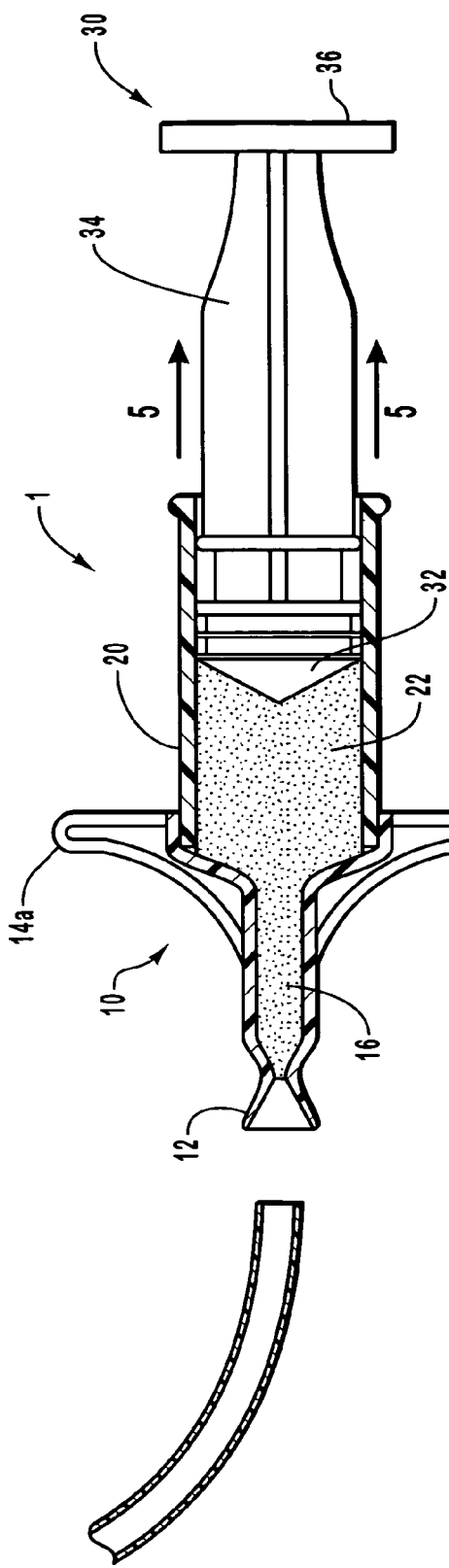
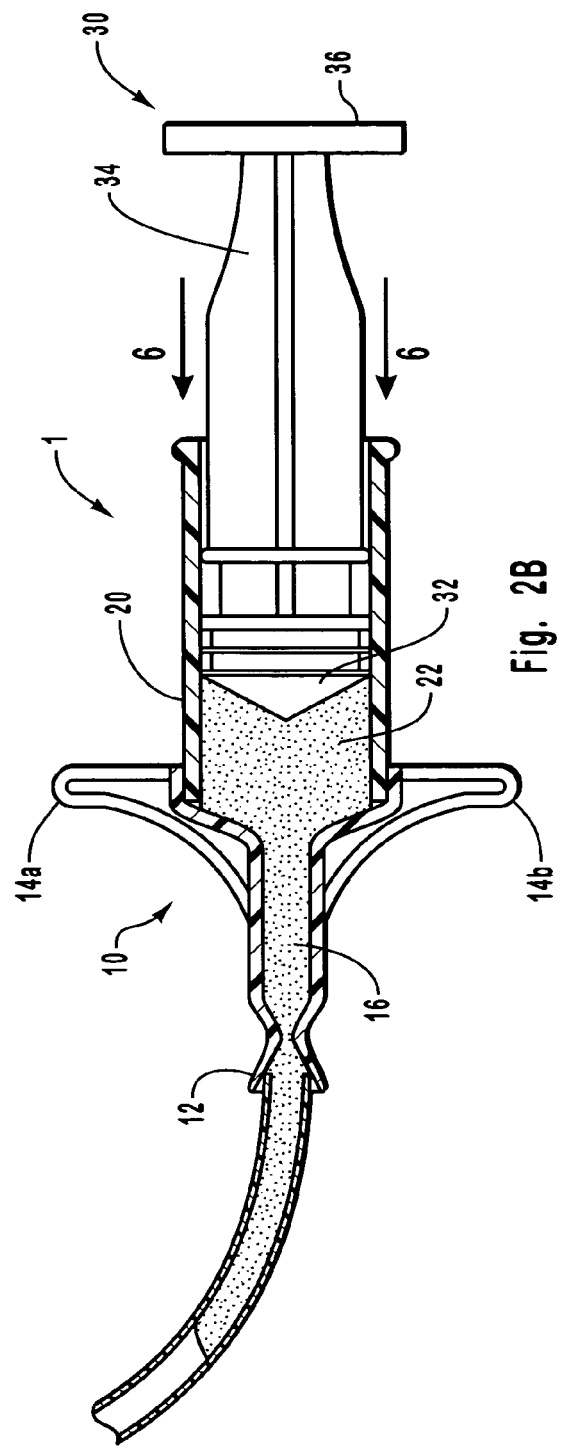
Fig. 2A
Fig. 2B

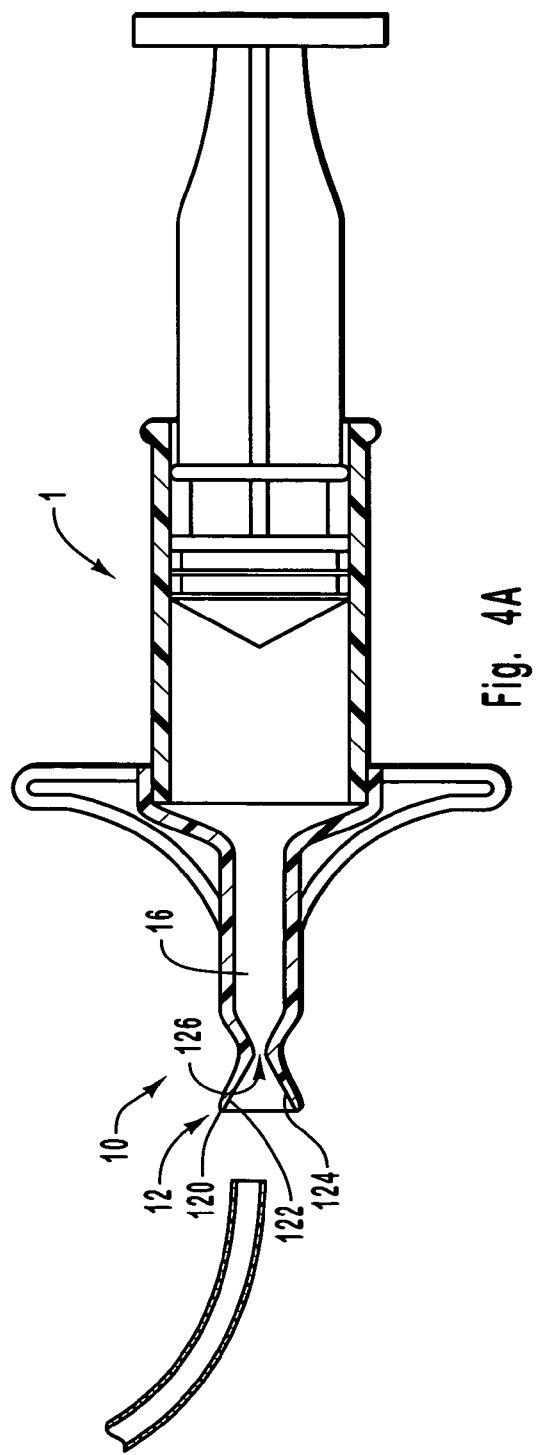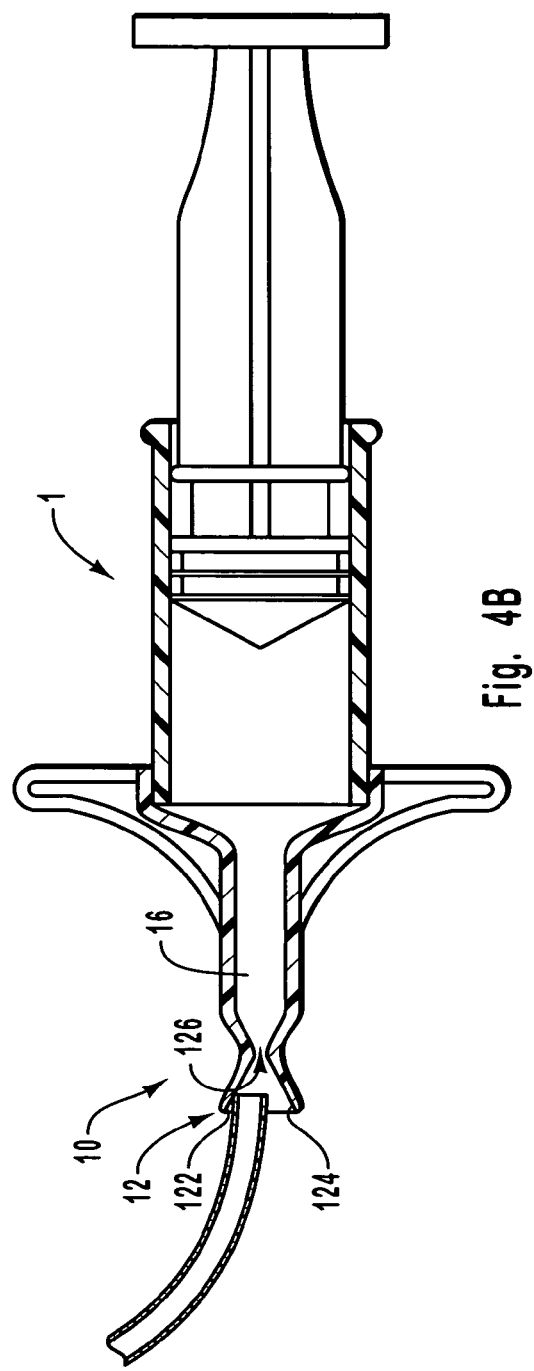

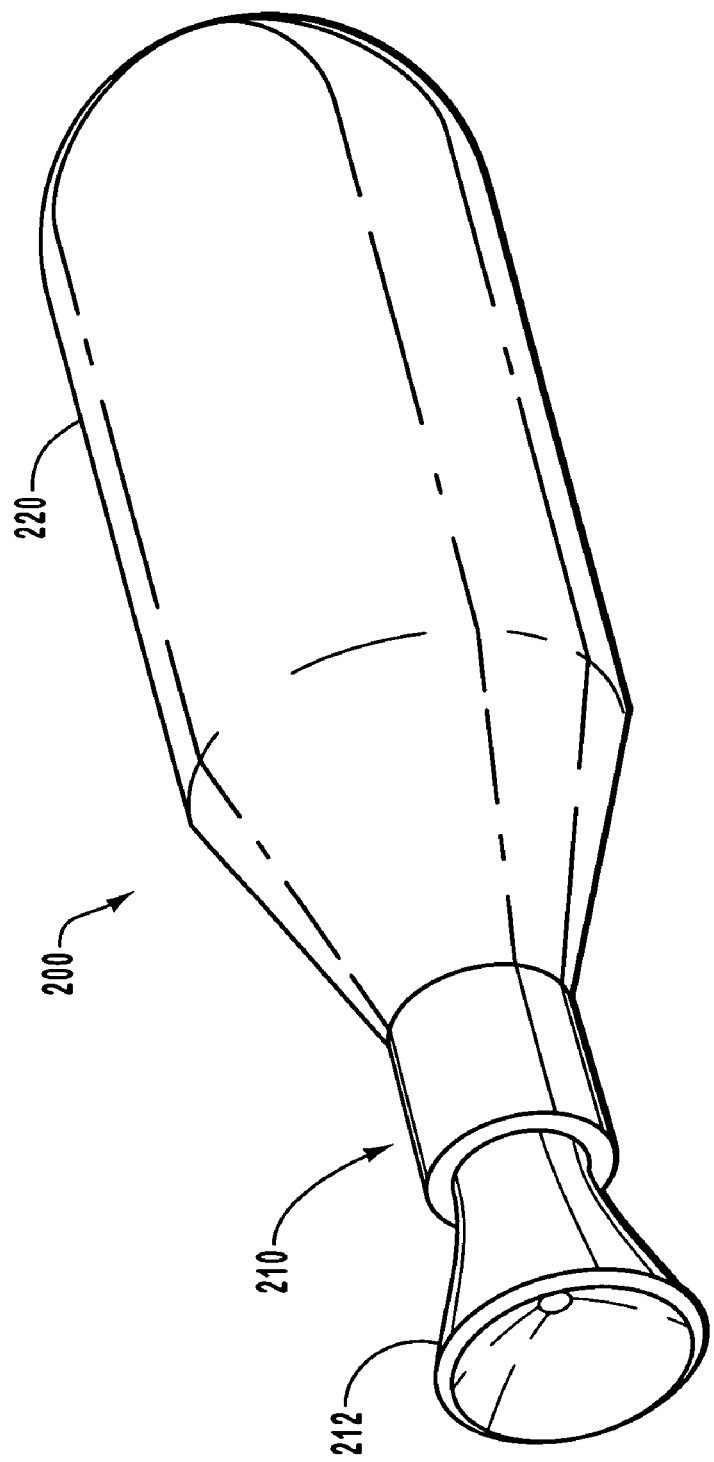

INTEGRAL FLUSHING DEVICE

BACKGROUND OF THE INVENTION

1. The Field of the Invention

The present invention relates to flushing devices. In more particular, the present invention relates to a flushing device having one-handed operability.

2. The Relevant Technology

Flushing devices are used in the medical product industry to inject liquid or other medicines and materials into the lumen of a catheter. Injecting materials into the lumen of a catheter can perform a variety of helpful and necessary functions in the use of the catheter. For example, flushing the catheter may clear the catheter lumen of obstructions, fluids, and/or other materials that may have been introduced when inserting the catheter into a vessel of the patient. Such articles, fluids, and/or materials can occlude the passage way of the catheter lumen preventing or interfering with proper function of the catheter. Additionally, flushing the lumen can provide lubrication facilitating introduction of a guidewire or stent into the catheter lumen.

A variety of types and configurations of devices have been utilized by practitioners for flushing the lumen of a catheter. Many devices utilized for flushing the lumen of a catheter are little more than syringes, or other unspecialized apparatuses that have been slightly modified for the use of flushing a catheter. For example, one exemplary device comprises a syringe with a shortened needle tip. The needle tip is inserted into the lumen of the catheter and the catheter is flushed by depressing the plunger of the syringe to force fluids through the lumen of the catheter. Utilizing such a device for flushing a catheter can be a crude solution for flushing a catheter. This is because the tip of the needle must be carefully introduced into the lumen of the catheter. This can require dexterity and attentiveness that may detract from other aspects of a procedure to be performed. Additionally, the contact between the syringe and the catheter can result in an incomplete seal resulting in spraying or loss of the flushing medium when the plunger is depressed. This can decrease the ability of the medium to adequately clear the catheter lumen from obstructions, fluids, and/or other materials in the intended manner.

Another exemplary device utilizes a syringe in connection with a flushing tip. The flushing tip includes threads or a luer coupling allowing the flushing tip to be attached at the end of the syringe. One problem associated with such tips, is that the configuration of the aperture in which the catheter is inserted can make guiding the catheter into the aperture problematic. Additionally, the catheter tips are typically opaque making it difficult to monitor progress of the catheter into the tip. Such syringes are typically unnecessarily large due to the size of the luer coupler needed to receive the flushing tip. The size of the catheter can affect the ability of the user to manipulate the plunger barrel utilizing a single hand. Additionally, the amount of flushing medium held in the barrel can be excessive for what is needed or desired for the flushing procedure to be performed. The excessive amount of flushing medium can make it difficult to manipulate the catheter while simultaneously controlling the amount of flushing medium being injected into utilizing the flushing device, particularly where flushing of the catheter is only part of a more complex procedure to be performed.

BRIEF SUMMARY OF THE INVENTION

The present invention relates to a flushing device having simple operation and one-handed control. The flushing device utilizes a plunger for expelling a flushing medium from the barrel of the flushing device. The plunger is configured such that the user can actuate the plunger easily with the user's palm and/or with other portions of the user's hand. The flushing device includes a receiving tip which has a distal end and a proximal end. The inner diameter of the distal end of the receiving tip is larger than the inner diameter of the proximal end of the receiving tip. This provides a conical configuration that allows the user to easily insert the catheter tip into the receiving tip while also facilitating an air tight seal between the receiving tip and the tip of the catheter. In one embodiment, the receiving tip is non-opaque (i.e. clear, translucent) to allow the user to view insertion of the catheter tip. In another embodiment, the receiving tip is integrally coupled to other components of the flushing device to ensure simple operation of the flushing device.

The flushing device includes one or more finger grips positioned adjacent the receiving tip of the flushing device. The one or more finger grips allow the user to operate the flushing device using a single hand. The position of the one or more finger grips allows the user to control movement of the receiving tip facilitating ease of insertion of the catheter tip into the receiving tip. Additionally, the finger grips allow the user to control the movement of the receiving tip while compressing the plunger. In one embodiment, the one or more finger grips are positioned distally from a middle portion of the barrel.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2A is a cross-sectional side view of the flushing device illustrating the plunger being withdrawn to allow filling of the flushing device according to one embodiment of the present invention.

FIG. 2B is a cross-sectional side view of the flushing device illustrating the plunger being depressed to force fluid into a lumen of a catheter, according to one embodiment of the present invention.

FIG. 4A is a cross-sectional side view of the flushing device illustrating a catheter tip being advanced toward the receiving tip of the flushing device according to one aspect of the present invention.

FIG. 4B is a cross-sectional side view of the flushing device illustrating a catheter tip in contact with one side of the internal diameter of the receiving tip according to one aspect of the present invention.

FIG. 6 is a perspective view of an alternative configuration of the flushing device having a compressible bulbous portion for holding and flushing medium from the flushing device according to one aspect of the present invention.

DETAILED DESCRIPTION OF THE PREFERRED EMBODIMENTS

The present invention relates to a flushing device having simple operation and one-handed control. The flushing device utilizes a plunger for expelling a flushing medium from the barrel of the flushing device. The plunger is configured such that the user can actuate the plunger easily with the user's palm and/or with other portions of the user's hand. The flushing device includes a receiving tip which has a distal end and a proximal end. The inner diameter of the distal end of the receiving tip is larger than the inner diameter of the proximal end of the receiving tip. This provides a conical configuration that allows the user to easily insert the catheter tip into the receiving tip while also facilitating an air tight seal between the receiving tip and the tip of the catheter. In one embodiment, the receiving tip is non-opaque (i.e. clear, translucent) to allow the user to view insertion of the catheter tip. In another embodiment, the receiving tip is integrally coupled to other components of the flushing device to ensure simple operation of the flushing device.

The flushing device includes one or more finger grips positioned adjacent the receiving tip of the flushing device. The one or more finger grips allow the user to operate the flushing device using a single hand. The position of the one or more finger grips allows the user to control movement of the receiving tip facilitating ease of insertion of the catheter tip into the receiving tip. Additionally, the finger grips allow the user to control the movement of the receiving tip while compressing the plunger. In one embodiment, the one or more finger grips are positioned distally from a middle portion of the barrel.

Figure 1:
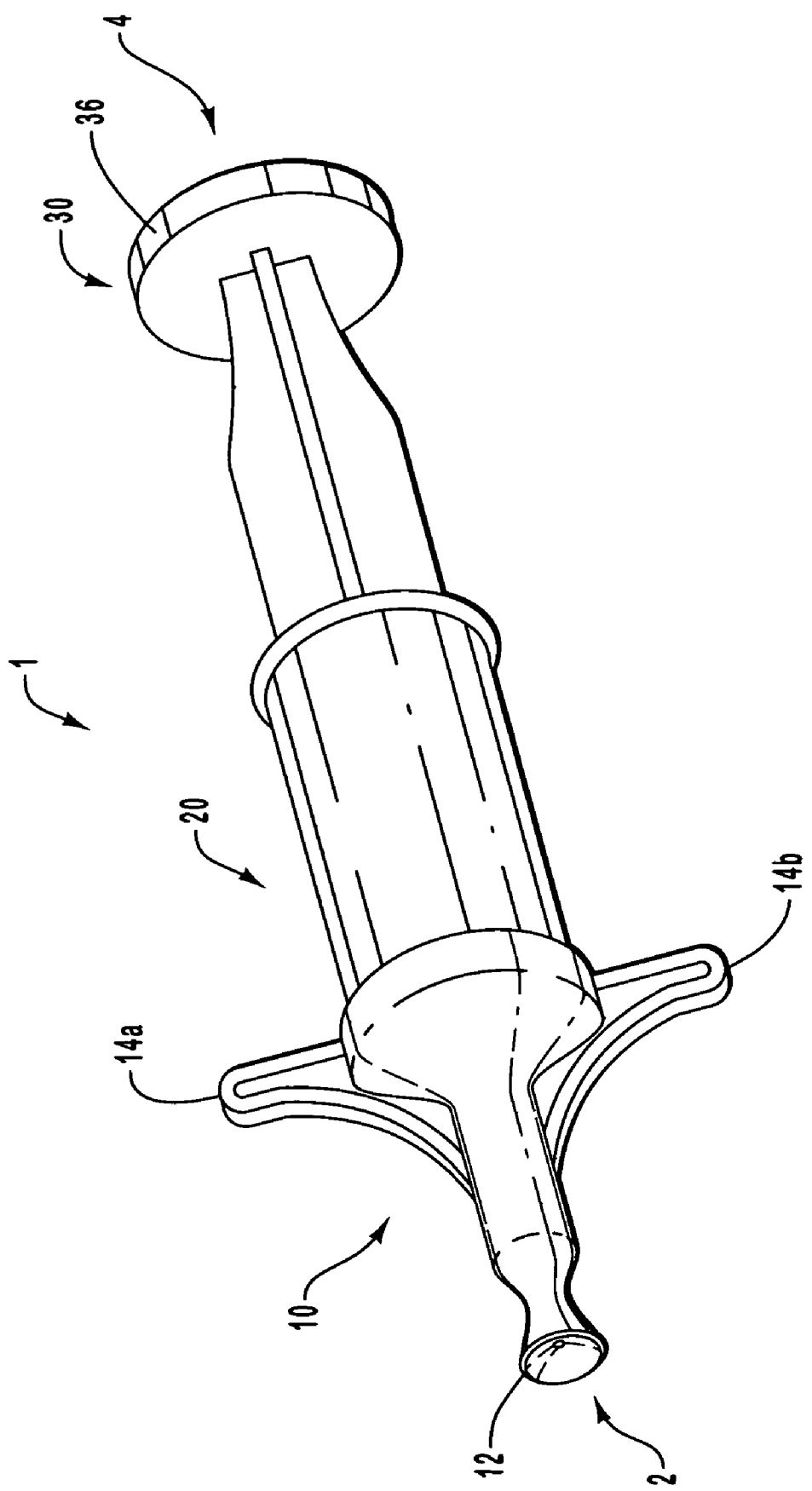
FIG. 1 is a perspective view of a flushing device according to one embodiment of the present invention.

FIG. 1 is a perspective view of the flushing device according to one aspect of the present invention. In the illustrated embodiment the flushing device includes a flushing portion 10, a barrel 20, and a plunger 30. Flushing portion 10 is utilized to interact with a tip of a catheter and to direct the flow of flushing medium from barrel 20 into the lumen of a catheter. Barrel 20 comprises a portion of the body of flushing device 1 while also providing a receptacle for holding a flushing medium. Plunger 30 comprises a mechanism for expelling the flushing medium from the barrel 20. In the illustrated embodiment, the plunger 30 is configured such that a user can actuate plunger 30 with the user's palm. In the illustrated embodiment, plunger 30 includes a palm press member 36.

In the illustrated embodiment, flushing portion 10 includes a receiving tip 12 and finger grips 14a, b. Receiving tip 12 is positioned at the distal end 2 of the flushing device 1. In the illustrated embodiment, receiving tip 12 forms a conical funnel facilitating mating of a catheter tip with the receiving tip 12 of flushing device 1. Receiving tip 12 is one example of a flushing tip according to one aspect of the present invention.

Finger grips 14a, b are positioned between distal end 2 of flushing device 1 and proximal end 4 of flushing device 1. In the illustrated embodiment, finger grips 14a, b are positioned at the distal end of barrel 20. Finger grips 14a, b provide a mechanism allowing a user to grasp flushing device 1 in a controlled and advantageous manner. In the illustrated embodiment, finger grips 14a, b comprise projections which extend from the lateral sides of flushing device 1. As will be appreciated by those skilled in the art, a variety of types and configurations of finger grips can be utilized without departing from the scope and spirit of the present invention. For example, in one embodiment, the finger grips comprise circular rings which extend from the lateral sides of flushing device 1 allowing a user to insert the user's fingers therethrough. In another embodiment, the finger grips comprise anti-skid members which allow the user to grip the flushing device without slippage of the flushing device. In another embodiment, the finger grips comprise a portion of the barrel that is graspable by the user.

The one or more finger grips are positioned between a middle portion of barrel 20 and receiving tip 12. The positioning of finger grips 14a, b allows a user to operate flushing device 1 utilizing a single hand. To operate flushing device, a user places two fingers (e.g. index finger and ring finger) alternatively on finger grips 14a, b. The user then positions a thumb or the palm of the user's hand against plunger 30. By compressing plunger 30, flushing medium moves from barrel 20 and is expelled from receiving tip 12. Where the tip of a catheter is in fluid tight connection with receiving tip 12, the flushing medium is forced into the lumen of the catheter effectively flushing the catheter.

According to one embodiment of the present invention, the distance between the receiving tip and the palm press member is less than 4.25 inches when the plunger is in an extended position. In another embodiment, the distance between the receiving tip and the palm press member is less than 4 inches when the plunger is in an extended position. In another embodiment, the distance between the receiving tip and the palm press member is about 3.5 inches when the plunger is in an extended position.

In one embodiment, the distance between the receiving tip and the palm press member is less than 4 inches when the plunger is in an depressed position. In another embodiment, the distance between the receiving tip and the palm press member is less than 3 inches when the plunger is in a depressed position. In another embodiment, the distance between the receiving tip and the palm press member is about 2.7 inches when the plunger is in a depressed position. In another embodiment, the distance between the one or more finger grips and the palm press member is less than 3 inches when the plunger is in an extended position.

FIG. 2A is a side cross-sectional view of flushing device 1 illustrating operability of flushing device 1. In the illustrated embodiment, directional arrows 5-5 illustrate the movement of plunger 30. The configuration of flushing device 1 allows a user to draw up a flushing medium utilizing a single hand. The distance between the finger grips 14a, b and plunger 30 allows the user to retract plunger 30 from lumen 22 of barrel 20 using the same hand with which the user is holding the flushing device 1. For example, the user can grip finger grips 14a, b with the user's index and middle finger while retracting the plunger using the thumb of the user's same hand.

As plunger 30 is retracted from a storage lumen 22 of barrel 20 a vacuum is created in storage lumen 22 allowing the movement of flushing lumen into storage lumen 22. In the illustrated embodiment, movement of plunger 30 is at or near its proximal most orientation. When plunger 30 is at or near its proximal most orientation, storage lumen 22 is at or near its flushing medium filling capacity.

In one embodiment, storage lumen 22 is filled with flushing medium by placing receiving tip 12 in a reservoir of flushing medium and withdrawing plunger 30 from storage lumen 22. A plunger sealing tip 32 of plunger 30 provides an air tight connection between plunger 30 and the inside diameter of barrel 20. The air tight seal between plunger sealing tip 32 and the inside diameter of barrel 20 creates a vacuum or siphoning effect when plunger 30 is withdrawn. The vacuum or siphoning effect results in movement of flushing medium from the flushing medium reservoir through receiving tip 12, into a flushing lumen 16 positioned between receiving tip 12 and storage lumen 22, and finally into storage lumen 22.

FIG. 2B is a cross-sectional side view of flushing device 1 illustrating operability of flushing device 1. In the illustrated embodiment, directional arrows 6-6 illustrate movement of plunger 30 for expelling the flushing medium from storage lumen 22. A catheter tip is positioned in fluid connection with receiving tip 12. This allows movement of flushing medium from receiving tip 12 into the lumen of the catheter.

A user expels flushing medium from flushing device 1 by exerting force on palm press member 36 in the direction of arrows 6. As plunger sealing tip 32 moves in the distal direction, fluid tight coupling between plunger sealing tip 32 and the inner diameter of barrel 20 prevents or minimizes leakage of fluid from the proximal end of barrel 20. Movement of plunger sealing tip 32 and the distal direction forces flushing medium from storage lumen 22, through flushing lumen 16, out receiving tip 12, and into the lumen of the catheter.

As will be appreciated by those skilled in the art, a variety of types and configurations of flushing devices can be utilized without departing from the scope and spirit of the present invention. For example, in one embodiment, the flushing device provides a secondary mechanism for allowing filling of the storage lumen from a point other than the receiving tip. In another embodiment, a mechanism other than a plunger is utilized to fill and/or expel flushing medium from storage lumen 22.

Figure 3:
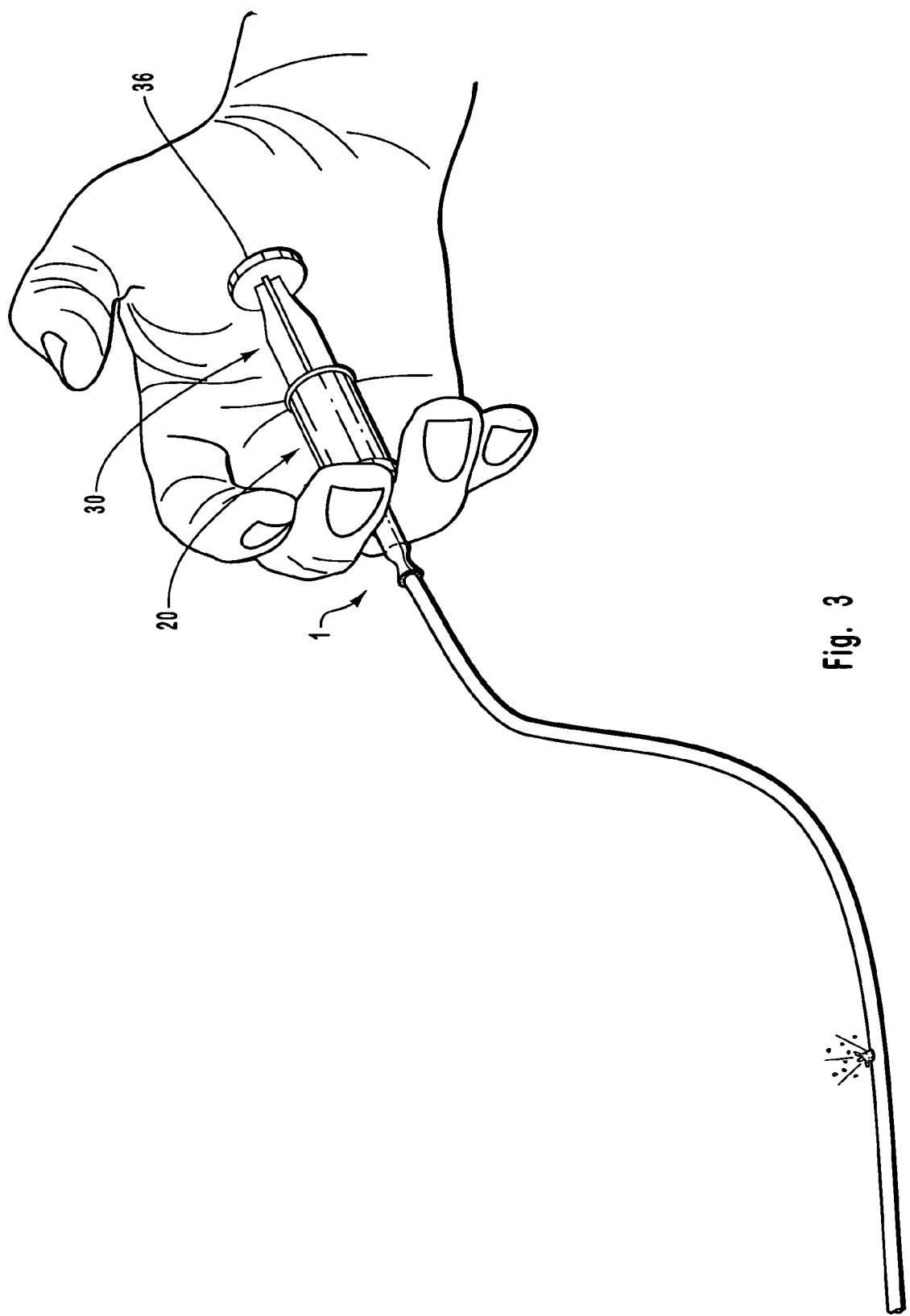
FIG. 3 is a perspective view of a flushing device illustrating operation of flushing device with respect to a catheter according to one aspect of the present invention.

FIG. 3 is a perspective view of flushing device 1 being utilized with a catheter illustrating the operability of flushing device 1 with a catheter. In the illustrated embodiment, a user is holding flushing device 1 utilizing a single hand. The user's ring finger is positioned over finger grips 14b while the user's middle finger is positioned over the alternative finger grip 14a. The palm press member 36 of plunger 30 is positioned in the user's palm. By simply flexing the user's hand, plunger 30 can be pushed in the distal direction. The tip of the catheter is positioned in receiving tip 12. An aperture in the side wall of the catheter allows catheter flushing medium to be expelled therefrom as the user compresses plunger 30 of flushing device 1. The aperture in the side of the catheter wall allows release of the fluid once the flushing medium has reached a predetermined point in the catheter lumen. While not shown for the sake of clarity, the user's other hand will often be used to grasp the catheter tip to maintain the connection between receiving tip 12 and the catheter tip.

FIG. 4A is a cross-sectional side view of flushing device 1 illustrating operation of receiving tip 12 relative to the tip of the catheter. Receiving tip 12 comprises an outer rim 120, an inner surface first portion 122, an inner surface second portion 124, and an inner bore 126. The inner diameter of the distal end of receiving tip 12 is larger in diameter than the inner diameter of the proximal end of receiving tip 12. This provides a tapered configuration facilitating introduction of the catheter tip into receiving tip 12. The inner diameter of the distal end is sufficiently large to easily align the catheter tip with the inner diameter of receiving tip 12. The tapered configuration allows the catheter tip to connect with and provide a fluid tight coupling with an inner diameter of receiving tip 12. As shown in FIG. 4A the catheter tip is shown approaching receiving tip 12. The inner diameter of the distal end of receiving tip 12 is substantially larger than the catheter tip. This allows the user to easily align the catheter tip with the receiving tip 12 without distracting from other aspects of the procedure being performed.

FIG. 4B shows the catheter tip that has been advanced within inside the outer rim 120 of receiving tip 12. The catheter tip while not centrally aligned with receiving tip 12 is nonetheless circumscribed by the outer rim 120 of receiving tip 12. The catheter tip is contacting the inner surface of first portion 122 while being positioned away from the inner surface of second portion 124.

Figure 4C:
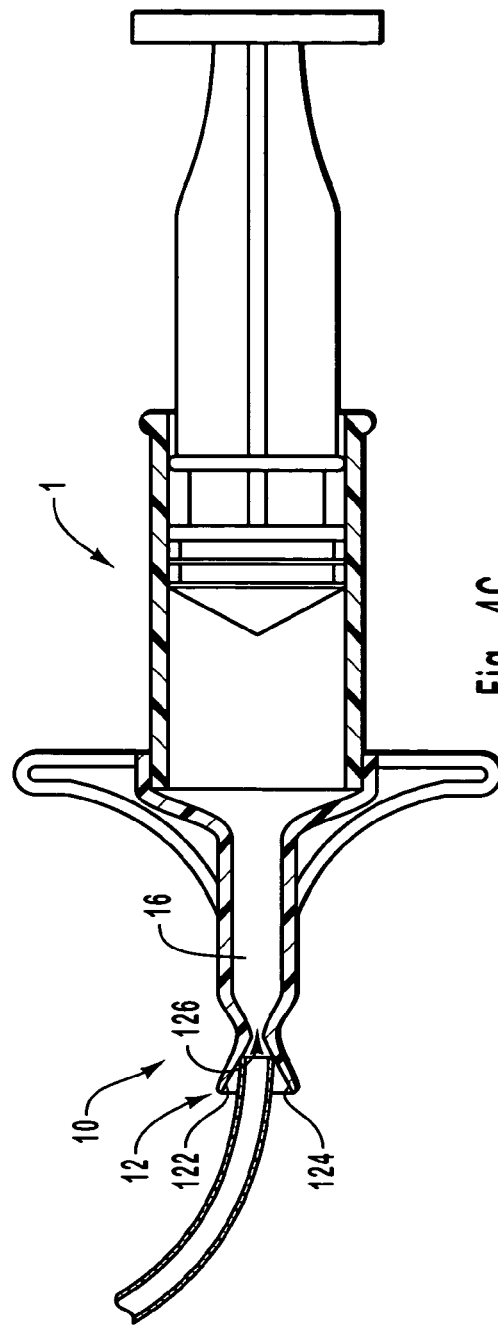
FIG. 4C is a cross-sectional side view of the flushing device illustrating a catheter tip in fluid connection with the internal diameter of the receiving tip of the flushing device according to one aspect of the present invention.

FIG. 4C illustrates that as the user continues to advance the catheter tip toward the inner bore of receiving tip 12, the tapered configuration of the inner surface first portion 122 causes the catheter tip to slide toward inner bore 126 and into engagement with inner surface second portion 124. The engagement with inner surface second portion 124 occurs when the inner diameter of receiving tip 12 is substantially the same as the outer diameter of the catheter tip. In this manner the tapered configuration of the receiving tip 12 provides for a advantageous and efficient connection between receiving tip 12 and the catheter tip.

Figure 5:
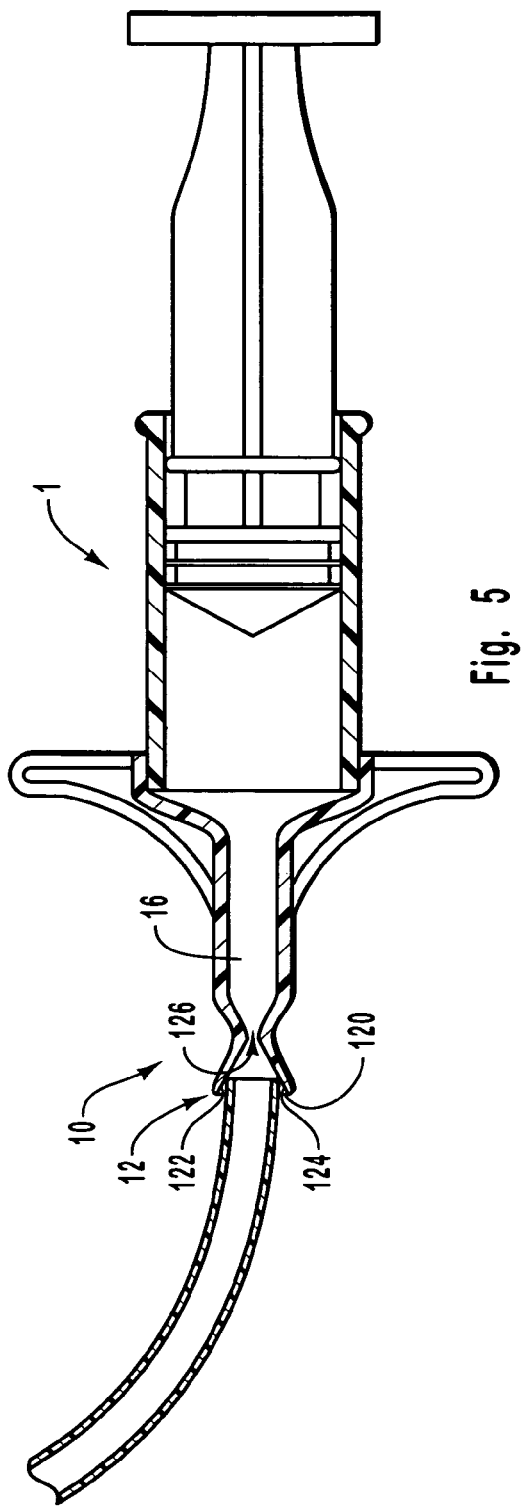
FIG. 5 is a cross-sectional side view of the flushing device illustrating a catheter tip of a larger bore being utilized in connection with a flushing device according to one aspect of the present invention.

FIG. 5 illustrates flushing device 1 utilized in connection with a catheter having a larger diameter. The tapered configuration of receiving tip 12 allows for the fluid tight connection of the catheter tip and the inner surface of receiving tip 12. In this manner, a receiving tip having a single size and configuration can be utilized with catheters having a plurality of different sizes. This allows the hospitals, practitioners, and suppliers to buy and sell a smaller number of flushing devices for use with a large number of catheters of different diameters. For example, a single flushing device having a large amount of tapering can be utilized for all diameters of catheters. This can result in a streamlining of medical device purchasing and storage, as well as large cost savings. For example, a single flushing device can be utilized in prepackaging with a number of different catheters in combination with other devices.

FIG. 6 illustrates a disposable flushing device 200. Disposable flushing device 200 provides a simple and efficient configuration that can be utilized to flush the lumen of a catheter. Additionally, disposable flushing device 200 can be manufactured simply and cost effectively to be utilized in areas where the economic realities and/or manufacturing capabilities dictate a simpler and more cost effective design.

In the illustrated embodiment, disposable flushing device 200 comprises a proximal flushing portion 210, a receiving tip 212, and a compressible bulbous portion 220. In the illustrated embodiment, the compressible bulbous portion 220 is configured to both hold a flushing medium while also allowing expulsion of the flushing medium from the disposable flushing device 200. Proximal flushing portion 210 provides a point of coupling between receiving tip 212 and compressible bulbous portion 220. Receiving tip 212 provides a conical tapered tip for receiving a catheter tip. In one embodiment, the receiving tip 212 can be quickly and easily inserted in a compressible fashion with the proximal flushing portion to provide the coupling required for operation of a disposable flushing device 200.

A user operates disposable flushing device 200 by compressing bulbous portion 220. Once the user compresses compressible bulbous portion 220, the user inserts receiving tip 212 into reservoir of flushing medium. The user then releases compressible bulbous portion 220 allowing compressible bulbous potion 220 to return to its previous form. When compressible bulbous portion 220 returns to its original form, flushing medium is drawn from the flushing medium reservoir, into receiving tip 212 and finally into compressible bulbous portion 220. When compressible bulbous portion 220 is filled with flushing medium, the user can place the catheter tip into receiving tip 212 in a manner similar to that illustrated with respect to flushing device 1 of FIGS. 1-5. The user then compresses compressible bulbous portion 220 forcing the flushing medium from compressible bulbous portion 220 through receiving tip 212 and into the catheter tip.

The configuration of disposable flushing device 200 allows a user to operate the disposable flushing device 200 utilizing a single hand. This allows the user to effectively manipulate the catheter tip with the user's other free hand. According to one embodiment of the present invention, disposable flushing device 200 is non-opaque (e.g. clear, translucent) to allow a user to view filling of flushing medium into compressible bulbous portion, movement of catheter tip within receiving tip 212, and expelling of flushing medium from disposable flushing device 200 into the catheter lumen.

As will be appreciated by those skilled in the art, a variety of types and configurations of flushing devices can be utilized without departing from the scope and spirit of the present invention. For example, in one embodiment, the flushing device is formed as a single integral mechanism. In another embodiment, the mechanism for expelling a flushing medium from the receptacle for holding the flushing medium is utilized that does not comprise a compressible bulbous portion or a plunger. In another embodiment, the flushing device utilizes a receiving tip that is not conical and/or tapered in nature. In another embodiment, the length of the barrel of the flushing device allows the user to operate the disposable flushing device using a single hand.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A flushing device having a proximal end and a distal end utilized to flush a catheter, the flushing device comprising:
   a receptacle for holding a flushing medium;
   a mechanism for expelling the flushing medium from the receptacle;
   a flushing tip positioned at the distal end of the flushing device, the flushing tip having a distal end, a proximal end and a tapered inner contact surface aligned to be contacted by a catheter to be flushed, wherein an inner diameter of the distal end of the flushing tip is larger than a diameter of the catheter to be flushed and an inner diameter of the proximal end is smaller than the diameter of the catheter to be flushed such that when a tip of the catheter contacts a portion of the tapered inner contact surface the catheter tip is moved relative to the inner contact surface to align the catheter tip into desired engagement with an internal diameter of the contact surface and the catheter tip is circumscribed by an outer rim of the flushing tip, and wherein the distance between the flushing tip and the mechanism for expelling the flushing medium is less than 4.25 inches when the mechanism for expelling the flushing medium is in an extended position; and
   one or more gripping portions positioned distally from a middle portion of the receptacle.

2. The flushing device of claim 1, wherein the receptacle for holding a flushing medium comprises barrel.

3. The flushing device of claim 1, wherein the mechanism for expelling the flushing medium comprises a plunger.

4. The flushing device of claim 1, wherein the receptacle for holding a flushing medium comprises a barrel and the mechanism for expelling the flushing medium comprises a plunger, and wherein the plunger is disposed within the barrel.

5. The flushing device of claim 4, wherein the user depresses the plunger to expel flushing medium from the barrel.

6. The flushing device of claim 1, wherein the flushing tip comprises a receiving tip.

7. The flushing device of claim 1, wherein the receptacle for holding a flushing medium comprises a bulb.

8. The flushing device of claim 1, wherein the receptacle for holding a flushing medium and the mechanism for expelling the flushing medium comprises a single compressible bulb.

9. The flushing device of claim 1, wherein the one or more gripping portions comprise one or more finger grips.

10. A flushing device having one handed operability, the flushing device comprising:
    a barrel for holding a flushing medium;
    a plunger for expelling the flushing medium from the receptacle, the plunger being configured such that a user can actuate the plunger with the user's palm;
    a receiving tip positioned at a distal end of the flushing device, the receiving tip having a distal end, a proximal end and a tapered inner contact surface aligned to be contacted by a catheter to be flushed, wherein an inner diameter of the distal end of the receiving tip is larger than a diameter of the catheter to be flushed and an inner diameter of the proximal end is smaller than the diameter of the catheter to be flushed such that when a tip of the catheter contacts a portion of the tapered inner contact surface the catheter tip is moved relative to the inner contact surface to align the catheter tip into desired engagement with an internal diameter of the contact surface and the catheter tip is circumscribed by an outer rim of the receiving tip, and wherein the distance between the receiving tip and a proximal end of the plunger is less than 4.25 inches when the plunger is in an extended position; and
    one or more finger grips for allowing the user to control movement of receiving tip while compressing the plunger, the one or more finger grips positioned distally from a middle portion of the barrel.

11. The flushing device of claim 10, wherein the finger grips are positioned adjacent the receiving tip.

12. The flushing device of claim 10, wherein the finger grips are positioned laterally on opposite sides of the flushing device.

13. The flushing device of claim 10, wherein the finger grips comprise projections which extend from lateral sides of the barrel.

14. The flushing device of claim 10, wherein the finger grips comprise circular rings.

15. The flushing device of claim 14, wherein the circular rings extend from the lateral sides of the flushing device allowing a user to insert the user's fingers therethrough.

16. The flushing device of claim 15, wherein the finger grips comprise anti-skid members.

17. The flushing device of claim 16, wherein the finger grips allow the user to control the flushing device using a single hand.

18. A flushing device having one handed operability, the flushing device comprising:

a barrel for holding a flushing medium;

a plunger for expelling the flushing medium from the barrel, the plunger being configured such that a user can actuate the plunger with the user's palm;

a receiving tip having a distal end, a proximal end and a tapered inner contact surface aligned to be contacted by a catheter to be flushed, wherein the inner diameter of the distal end is larger than the inner diameter of the proximal end, such that the inner diameter of the distal end is larger than the diameter of the catheter to be flushed and the proximal end is smaller than the diameter of the catheter to be flushed such that when a tip of the catheter contacts a portion of the tapered inner contact surface the catheter tip is moved relative to the inner contact surface to align the catheter tip into desired engagement with an internal diameter of the contact surface and the catheter tip is circumscribed by an outer rim of the receiving tip, and wherein the receiving tip is integrally coupled to the other components of the flushing device; and one or more finger grips positioned between a middle portion of the barrel and the receiving tip, the finger grips extending from lateral sides of the flushing device, wherein the length of the barrel allows a user to operate the flushing device using a single hand.

19. The flushing device of claim 18, wherein the one or more finger grips are positioned adjacent the receiving tip.

20. The flushing device of claim 18, wherein the plunger is configured such that a user can actuate the plunger with the user's thumb.

21. The flushing device of claim 18, wherein the one or more finger grips comprise two finger grips positioned on opposite sides of the barrel.

22. A flushing device having one handed operability, the flushing device comprising:

a barrel for holding a flushing medium;

a plunger having a palm press member for expelling the flushing medium from the receptacle, the plunger being configured such that a user can actuate the plunger with the user's palm;

a receiving tip having a distal end, a proximal end and a tapered inner contact surface aligned to be contacted by a catheter to be flushed, wherein an inner diameter of the distal end is larger than a diameter of the catheter to be flushed and an inner diameter of the proximal end is smaller than the diameter of the catheter to be flushed such that when a tip of the catheter contacts a portion of the tapered inner contact surface the catheter tip is moved relative to the inner contact surface to align the catheter tip into desired engagement with an internal diameter of the contact surface and the catheter tip is circumscribed by an outer rim of the receiving tip; and one or more finger grips positioned between a middle portion of the barrel and the receiving tip, wherein the distance between the receiving tip and the palm press member is less than 4.25 inches when the plunger is in an extended position.

23. The flushing device of claim 22, wherein the distance between the receiving tip and the palm press member is less than 4 inches when the plunger is in an extended position.

24. The flushing device of claim 22, wherein the distance between the receiving tip and the palm press member is about 3.5 inches when the plunger is in an extended position.

25. The flushing device of claim 24, wherein the distance between the receiving tip and the palm press member is about 2.7 inches when the plunger is in a depressed position.

26. The flushing device of claim 22, wherein the distance between the receiving tip and the palm press member is less than 4 inches when the plunger is in a depressed position.

27. The flushing device of claim 22, wherein the distance between the receiving tip and the palm press member is less than 3 inches when the plunger is in a depressed position.

28. A flushing device having one handed operability, the flushing device comprising:

a barrel for holding a flushing medium;

a plunger having a palm press member for expelling the flushing medium from the receptacle, the plunger being configured such that a user can actuate the plunger with the user's palm;

a receiving tip having a distal end, a proximal end and a tapered inner contact surface aligned to be contacted by a catheter to be flushed, wherein an inner diameter of the distal end is larger than a diameter of the catheter to be flushed and an inner diameter of the proximal end is smaller than the diameter of the catheter to be flushed such that when a tip of the catheter contacts a portion of the tapered inner contact surface the catheter tip is moved relative to the inner contact surface to align the catheter tip into desired engagement with an internal diameter of the contact surface and the catheter tip is circumscribed by an outer rim of the receiving tip; and one or more finger grips positioned between a middle portion of the barrel and the receiving tip, wherein the distance between the receiving tip and the palm press member is less than 3 inches when the plunger is in an depressed position.

29. A flushing device having one handed operability, the flushing device comprising:

a barrel for holding a flushing medium;

a plunger having a palm press member for expelling the flushing medium from the receptacle, the plunger being configured such that a user can actuate the plunger with the user's palm;

a receiving tip having a distal end, a proximal end and a tapered inner contact surface aligned to be contacted by a catheter to be flushed, wherein an inner diameter of the distal end is larger than a diameter of the catheter to be flushed and an inner diameter of the proximal end is smaller than the diameter of the catheter to be flushed such that when a tip of the catheter contacts a portion of the tapered inner contact surface the catheter tip is moved relative to the inner contact surface to align the catheter tip into desired engagement with an internal diameter of the contact surface and the catheter tip is circumscribed by an outer rim of the receiving tip; and one or more finger grips positioned between a middle portion of the barrel and the receiving tip, wherein the distance between the one or more finger grips and the palm press member is less than 3 inches when the plunger is in an extended position.

30. The flushing device of claim 29, wherein the distance between the finger grips and the palm press member is about 2.3 inches when the plunger is in an extended position.

31. A flushing device, the flushing device comprising:

a barrel for holding a flushing medium;

a plunger for expelling the flushing medium from the receptacle, the plunger being configured such that a user can actuate the plunger with the user's palm;

a receiving tip positioned at a distal end of the flushing device, the receiving tip having a distal end, a proximal end and a tapered inner contact surface aligned to be contacted by the catheter to be flushed, wherein an inner diameter of the distal end of the receiving tip is larger than a diameter of the catheter to be flushed and an inner diameter of the proximal end is smaller than the diameter of the catheter to be flushed such that when a tip of the catheter contacts a portion of the tapered inner contact surface the inner contact surface causes the catheter tip to move relative to the inner contact surface to align the catheter tip into desired engagement with an internal diameter of the contact surface and the catheter tip is circumscribed by an outer rim of the receiving tip, wherein the distance between the receiving tip and the plunger is less than 4.25 inches when the plunger is in an extended position; and one or more finger grips positioned between a middle portion of the barrel and the receiving tip, wherein the length of the barrel allows a user to operate the flushing device using a single hand.

* * * * *

UNITED STATES PATENT AND TRADEMARK OFFICE
CERTIFICATE OF CORRECTION

PATENT NO. : 7,591,805 B2
APPLICATION NO. : 10/800071
DATED : September 22, 2009
INVENTOR(S) : Fred P. Lampropoulos It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1595 days.

Signed and Sealed this

Twenty-first Day of September, 2010

David J. Kappos
*Director of the United States Patent and Trademark Office*